June 26, 1973 W. H. JESSEL, JR., ET AL Plant Pat. 3,368
CHRYSANTHEMUM PLANT
Filed Sept. 30, 1971 2 Sheets-Sheet 1
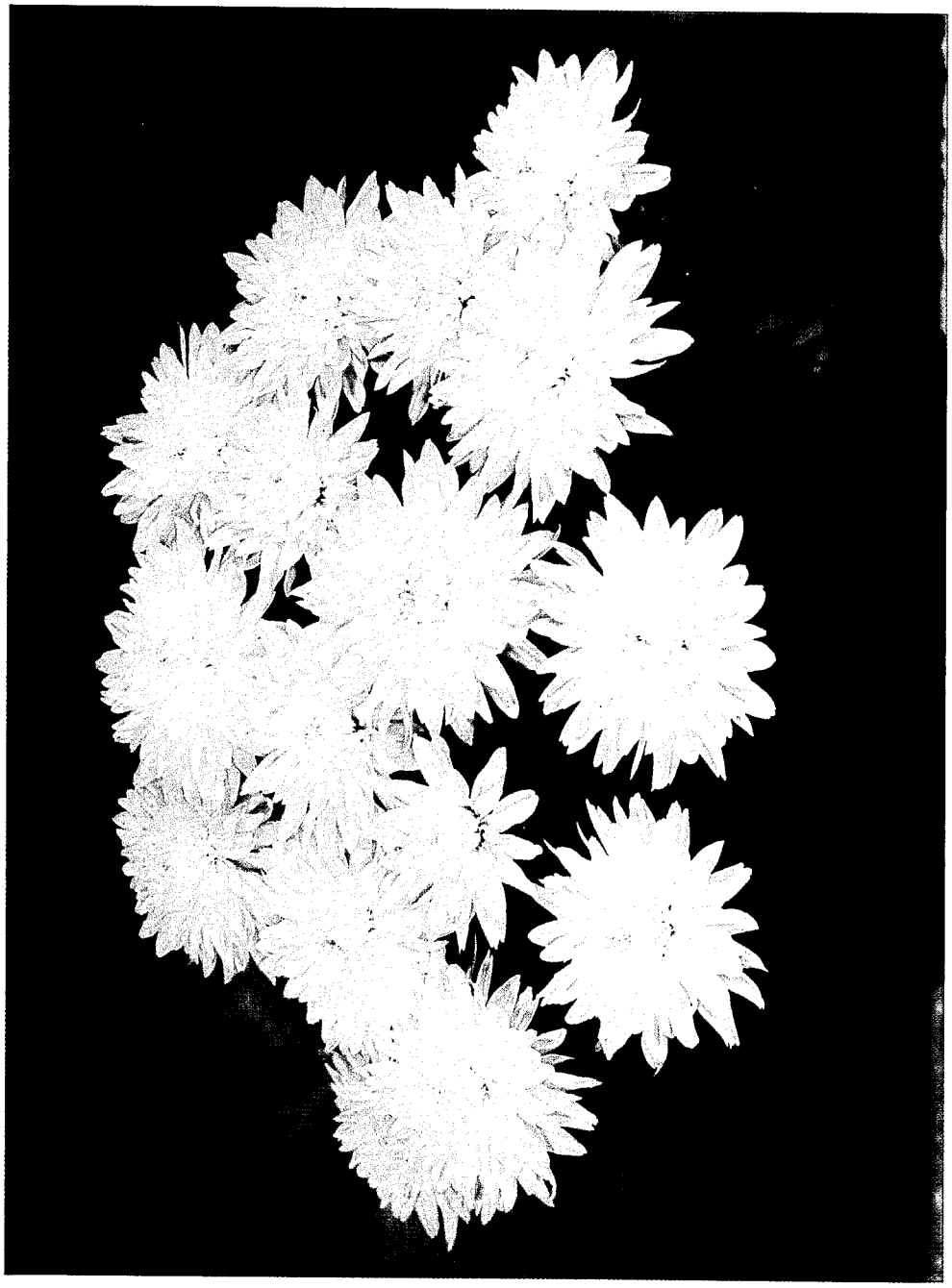

CHRYSANTHEMUM PLANT
Filed Sept. 30, 1971 2 Sheets-Sheet 2
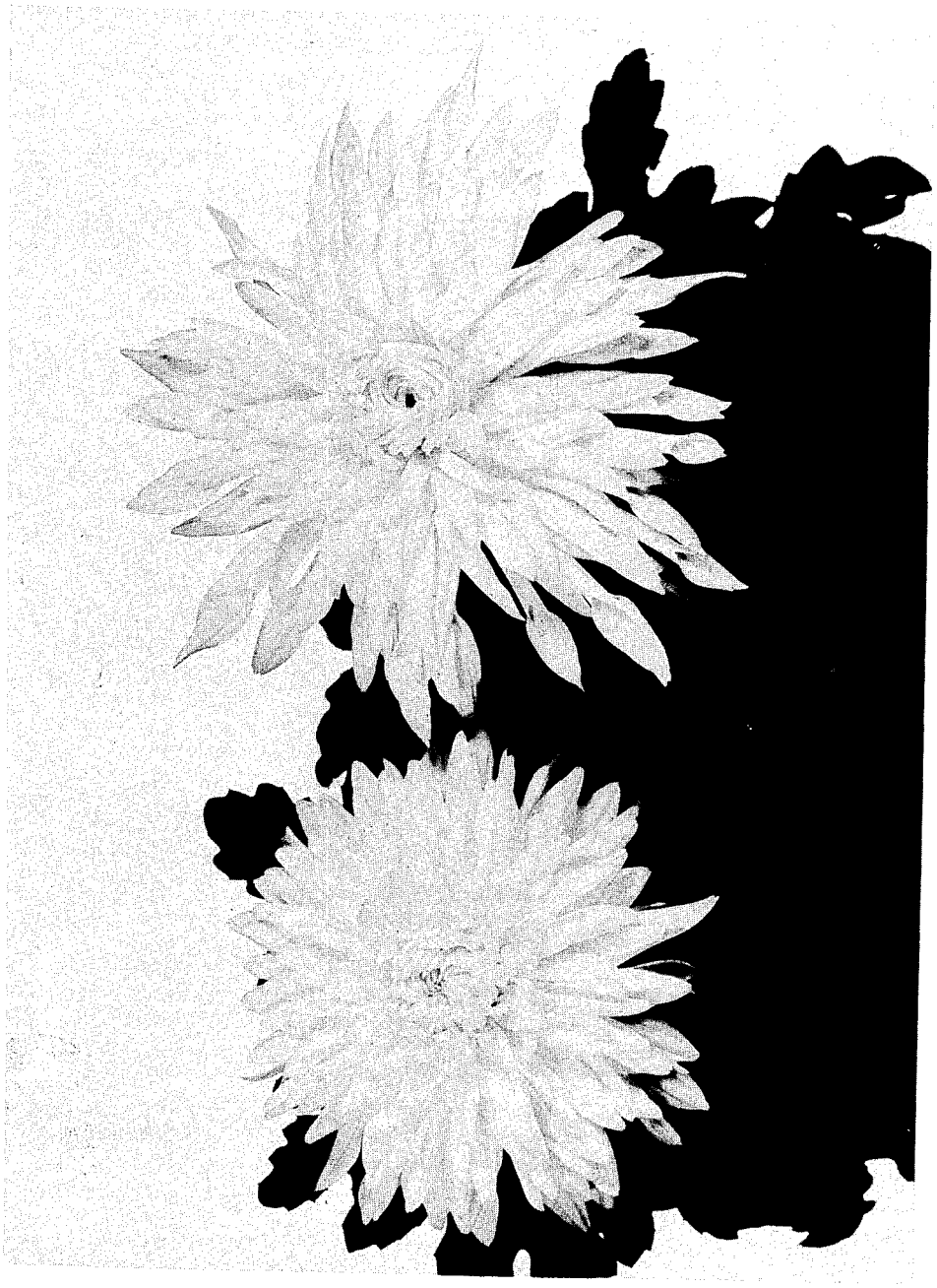

United States Patent Office

Plant Pat. 3,368

Patented June 26, 1973

3,368
CHRYSANTHEMUM PLANT

Walter H. Jessel, Jr., Doylestown, and William E. Duffett, Akron, Ohio, assignors to Yoder Brothers, Inc., Barberton, Ohio

Filed Sept. 30, 1971, Ser. No. 185,458
Int. Cl. A01h *5/00*
U.S. Cl. Plt.—77 1 Claim

The present invention comprises a new and distinct cultivar of chrysanthemum plant which is a seedling of #60228-2×#62966-1. Both parents are unpatented and identified for breeding purposes by the above numbers to distinguish the same from other parents in the breeding program.

The new cultivar is similar to the unpatented but commercially well known pot mum Neptune by virtue of its generally white flower color and decorative flower form, but is distinguished from Neptune by the following characteristics when grown under comparable conditions:

(1) Flowers are approximately one-half inch larger.

(2) Flowers provide approximately two to four days longer bench life.

(3) No pink tinging of the flowers at temperatures below 60° F.

(4) Broader, more ridged petals.

(5) No disc florets or pollen.

(6) Does not develop any longitudinal petal roll under low light conditions, which ages its appearance.

(7) Larger foliage, more coarse in texture and lighter in color, with a more coarse serration to the leaf margin.

(8) An approximately three inch more spread to a pinched plant in flower.

The new cultivar can also be compared with the commercially well known but unpatented Winter Carnival, similarly a decorative, white pot mum. The new cultivar is distinguished from Winter Carnival by its stronger, more compact, less upright plant habit, darker green foliage, smaller flower form but one with better symmetry and less reflexing, its pure white flower color that never tinges pink with a cool finish, and its approximately 5–7 days longer bench and home life.

The new cultivar was selected from the progeny of the designated cross and when asexually reproduced by cuttings at Barberton, Ohio, has been found to retain its distinctive characteristics through successive propagations.

The new cultivar when grown in the vicinity of Barberton, Ohio, has a response period of approximately 9 weeks, and the following detailed description is based on observations made of the new cultivar in a greenhouse in Barberton, Ohio. The response time, blooming period, color, and total vigor may vary significantly with varying environmental conditions such as temperature, daylength and light intensity.

This new cultivar can be flowered year-round in all areas of the United States. Its optimum flowering periods for the various areas is as follows: In the northern and western United States, October through May; south and southwestern United States, November through early May; coastal California, January through December, and in Florida, November through early May.

In accompanying drawings sheet 1 comprises a color photograph which shows the unique characteristics of the new cultivar, the color being as nearly true as possible with color illustrations of this type. Sheet 2 comprises a comparison photograph in black and white, with the new cultivar appearing on the left and the cultivar Winter Carnival on the right. The differences in flower form are readily visible.

In the description which follows, color references are made to the Munsell Color Book, 1963 edition, and comparisons are made with the cultivar Neptune. Where only a single value or description appears for the new cultivar, the same value or description applies as well to the comparison cultivar Neptune.

Botanical classification: *Chrysanthemum morifolium*

| | Paragon | Neptune |
|---|---|---|
| **Bloom:** | | |
| Size | 4½″ | 4″. |
| Fully expanded | 5½″ | 5″. |
| Borne | Terminal on disbudded stems | |
| Stems | Strong | |
| Form | Decorative | |
| Permanence | 12–16 days | |
| Color | Yellow green, 5GY9/2 | Streaked pink on white, 2.5RP5/12 with a cool finish of 60° F. or less, to white, 7.5Y9/2, at finishing temperatures above this level. |
| Base of petals | Yellow green, 5GY8/6 | N9.5/white. |
| Inside of petals | N9.5/white | |
| Reverse of petals | do | |
| Tonality from a distance | do | |
| Discoloration | N9.5/white, even at cool finishing temperatures below 60° F. | Streaked pink on white, 2.5RP5/12 with a cool finish of 60° F. or less, to white, 7.5Y9/2, at finishing temperatures above this level. |
| **Petals:** | | |
| Texture | Smooth | |
| Appearance and form | Closed at base, broadening to a shallow broad keel, tapering to a sharp point with recurved petal edges. | Slightly open at base, keeled at mid point, tapering to a point, several ridges on bottom 516″ wide. |
| Arrangement | Composite, whorled on a single receptacle | |
| Persistence | Resists shatter | |
| Fragrance | Typical chrysanthemum | |
| **Reproductive organs:** | | |
| Stamen, anthers | None | None to 25–30. |
| Pollen | do | None to scant. |
| Arrangement | Clustered in center of flower, if present | |
| Styles | Present ray florets | Present both ray and disc florets. |
| Length | Short | |
| Ovaries | At the base of petal attached to receptacle | |
| **Plant:** | | |
| Form | Herbaceous | |
| Growth | Spreading | Upright. |
| Height | Approximately 12″ when timed with 8 to 9 week medium treatment as outlined in the time-tables of Yoder Brothers, Inc., Barberton, Ohio. | Approximately 12″ when timed with 9 week short to medium treatment as outlined in the timetables of Yoder Brothers, Inc., Barberton, Ohio. |
| Spread | Approximately 8½″ as a pinched plant when timed with 8 to 9 week medium treatment as outlined in the timetables of Yoder Brothers, Inc., Barberton, Ohio. | Approximately 5½″ as a pinched plant when timed with 9 week short to medium treatment as outlined in the timetables of Yoder Brothers, Inc., Barberton, Ohio. |

Botanical classification: *Chrysanthemum morifolium*—Continued

| | Paragon | Neptune |
|---|---|---|
| Foliage: | | |
| Top side | Dark green, 5GY3/4 | Very dark green, 5GY2/4. |
| Size | 5″ long, 3½″ wide | 4″ long, 2½″ wide. |
| Quantity | Numerous | |
| Shape | Spatulate lobed | |
| Texture | Coarse | Smooth. |
| Ribs and veins | Moderately prominent | Prominent. |
| Edge | Moderately indented | Indented. |
| Serration | Coarse | Moderate. |
| Underside | Light green, 5GY5/4 | Light green, 10GY5/4. |
| Stipules | Prominent | |

We claim:

1. A new and distinct cultivar of chrysanthemum characterized particularly as to its uniqueness when compared to the cultivar Neptune by its flowers which are approximately one-half inch larger; flowers which provide approximately two to four days longer bench life; no pink tinging of the flowers at temperatures below 60° F.; broader, more ridged petals; no disc florets or pollen, no development of any longitudinal petal roll under low light conditions; larger foliage, more coarse in texture and lighter in color, with a more coarse serration to the leaf margin, and by its approximately three inch more spread to a pinched plant in flower; and characterized particularly as to uniqueness when compared to the cultivar Winter Carnival by its stronger, more compact, less upright plant habit; darker green foliage; a smaller flower form but one with better symmetry and less reflexing; pure white flower color that never tinges with a cool finish, and by its approximately 5–7 days longer bench and home life.

No references cited.

ROBERT E. BAGWILL, Primary Examiner

UNITED STATES PATENT OFFICE
CERTIFICATE OF CORRECTION

Plant
Patent No. 3,368 Dated June 26, 1973

Inventor(s) WALTER H. JESSEL, JR. and WILLIAM E. DUFFETT

It is certified that error appears in the above-identified patent and that said Letters Patent are hereby corrected as shown below:

In the tabulation below Columns 1 and 2, under "Petals:", opposite "Appearance and form", under "Neptune", "516" should be --5/16"--.

Signed and sealed this 1st day of October 1974.

(SEAL)
Attest:

McCOY M. GIBSON JR.
Attesting Officer

C. MARSHALL DANN
Commissioner of Patents

USCOMM-DC 60376-P69
* U.S. GOVERNMENT PRINTING OFFICE 1969 O—366-334